United States Patent [19]

Berg

[11] Patent Number: 5,599,979

[45] Date of Patent: Feb. 4, 1997

[54] SEPARATION OF FORMIC ACID FROM ACETIC ACID BY EXTRACTIVE DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 524,670

[22] Filed: Sep. 8, 1995

[51] Int. Cl.⁶ ................................................. C07C 51/42
[52] U.S. Cl. ........................... 562/608; 562/609; 562/606
[58] Field of Search ................................ 562/606, 608, 562/609

[56] References Cited

U.S. PATENT DOCUMENTS 1,813,636  7/1931  Petersen et al. .

4,692,219  9/1987  Berg .................................. 203/51

OTHER PUBLICATIONS

E. Lloyd Jones, "Economc Saving. . . Solvent Extraction", Chemistry and Industry, pp. 1590–1592.

Primary Examiner—Porfirio Nazario-Gonzalez
Assistant Examiner—Rosalynd A. Williams

[57] ABSTRACT

Formic acid is difficult to separate from acetic acid by conventional distillation or rectification because of the close proximity of their boiling points. Formic acid can be readily separated from acetic acid by using extractive distillation. Effective agents are propionic acid, butyric acid, valeric acid and 2-ethyl hexanoic acid.

2 Claims, No Drawings

SEPARATION OF FORMIC ACID FROM ACETIC ACID BY EXTRACTIVE DISTILLATION

FIELD OF THE INVENTION

This invention relates to a method for separating formic acid from acetic acid using certain organic compounds as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

Formic acid, B.P.=101° C. and acetic acid, B.P.=118° C. have a relative volatility of 1.23 and are difficult to separate by conventional rectification. Table 1 shows that to get 99% purity, sixty actual plates are required. For an agent giving a relative volatility of 1.55, only twenty-eight actual plates are required. An improvement of this magnitude represents a clear economic and operational advantage to the separation of these industrially important chemicals.

TABLE 1

Theoretical and Actual Plates Required vs. Relative Volatility for Formic Acid-Acetic Acid Separation

| Relative Volatility | Theoretical Plates Required At Total Reflux, 99% Purity | Actual Plates Required, 75% Eff. |
| --- | --- | --- |
| 1.23 | 45 | 60 |
| 1.50 | 23 | 31 |
| 1.55 | 21 | 28 |

OBJECTIVE OF THE INVENTION

The object of this invention is to provide a process or method of extractive distillation that will enhance the relative volatility of formic acid to acetic acid in their separation in a rectification column. It is a further object of this invention to identify certain organic compounds that are stable, are effective as extractive distillation agents and can be readily separated from formic acid or acetic acid and recycled to the extractive distillation column with little decomposition.

SUMMARY OF THE INVENTION

The objects of this invention are provided-by a process for the separation of formic acid from acetic acid which entails the use of certain organic compounds when-separately employed as the agent in extractive distillation.

TABLE 2

Effective Extractive Distillation Agents For Separating Formic Acid From Acetic Acid

| Compounds | Relative Volatility |
| --- | --- |
| None | 1.23 |
| Butyric acid | 1.65 |
| Valeric acid | 1.50 |
| 2-Ethyl hexanoic acid | 1.55 |
| Propionic acid | 1.45 |
| Propionic acid-Acetic acid | 1.60 |

DETAILED DESCRIPTION OF THE INVENTION

I have discovered that certain organic compounds will effectively increase the relative volatility between formic acid and acetic acid during rectification when employed as the agent in extractive distillation. Table 2 summarizes the data obtained with these agents. The agents which are effective are propionic acid, butyric acid, valeric acid and 2-ethyl hexanoic acid.

THE USEFULNESS OF THE INVENTION

The usefulness or utility of this invention can be demonstrated by referring to the data presented in Tables 1 and 2. All of the successful agents show that formic acid can be separated from acetic acid by means of extractive distillation in a rectification column and that the ease of separation as measured by relative volatility is considerable

WORKING EXAMPLES

Example 1: Thirty grams Of formic acid, 40 grams of acetic acid and 30 grams of 2-ethyl hexanoic acid were charged to a vapor-liquid equilibrium still and refluxed for three hours. Analysis indicated a vapor composition of 50.7% formic acid, 49.3% acetic acid; a liquid composition of 40.1% formic acid, 59.9% acetic acid. This is a relative volatility of formic acid to acetic acid of 1.55.

Example 2: Thirty-five grams of formic acid, 15 grams of acetic acid and 50 grams of propionic acid were charged to a vapor-liquid equilibrium still and refluxed for six hours. Analysis indicated a vapor composition of 32.6% formic acid, 32.0% acetic acid and 35.4% propionic acid; a liquid composition of 20.3% formic acid, 28.8% acetic acid and 50.9% propionic acid. This is a relative volatility of formic acid to acetic acid of 1.45; of formic acid to propionic acid of 2.3 and of acetic acid to propionic acid of 1.6.

I claim:

1. A method for recovering formic acid from a mixture of formic acid and acetic acid which comprises distilling a mixture of formic acid and acetic acid in a rectification column in the presence of about one part by weight of an extractive agent per part of formic acid-acetic acid mixture, recovering the formic acid as overhead product and obtaining the acetic acid and the extractive agent from the stillpot, wherein said extractive agent consists of one material selected from the group consisting of propionic acid, butyric acid, valeric acid and 2-ethyl hexanoic acid.

2. A method for recovering propionic acid from a mixture of propionic acid, formic acid and acetic acid which comprises distilling a mixture of propionic acid, formic acid and acetic acid in a rectification column, recovering the formic acid and the acetic acid as overhead product and obtaining the propionic acid from the stillpot.

* * * * *